United States Patent [19]

Wright et al.

[11] Patent Number: 4,565,831

[45] Date of Patent: Jan. 21, 1986

[54] PROCESS FOR PRODUCING AROMATIC HYDROCARBONS FROM CARBON MONOXIDE AND WATER

[75] Inventors: Franklin J. Wright, Watchung; Michael A. Richard, Fanwood; James C. Pirkle, Jr., Lebanon, all of N.J.

[73] Assignee: Exxon Research and Engineering Co., Florham Park, N.J.

[21] Appl. No.: 537,269

[22] Filed: Sep. 29, 1983

Related U.S. Application Data

[63] Continuation-in-part of Ser. No. 331,160, Dec. 16, 1981, abandoned.

[51] Int. Cl.⁴ ............................................. C07C 1/10
[52] U.S. Cl. ................................... 518/700; 518/711; 518/714; 518/717; 518/720; 518/721
[58] Field of Search ............... 518/711, 714, 721, 717, 518/720, 700; 585/408, 733, 469

[56] References Cited

U.S. PATENT DOCUMENTS

1,562,480 11/1925 Wietzel et al. .
2,711,420 6/1955 Brown et al. .
2,727,055 12/1955 Seelig et al. .
2,768,961 10/1956 Weck et al. .
2,815,357 3/1957 Seelig et al. .

FOREIGN PATENT DOCUMENTS

635950 6/1927 France .
300294 of 1928 United Kingdom .
866161 4/1961 United Kingdom .

*Primary Examiner*—Howard T. Mars
*Attorney, Agent, or Firm*—Robert J. North; Edward M. Corcoran

[57] ABSTRACT

A process is described using novel thallium-promoted iron catalysts in CO hydrogenation with steam. Mixtures of CO and steam are converted to liquid $C_6$–$C_{13}$ hydrocarbons containing substantial amounts of $C_6$–$C_{13}$ aromatics.

18 Claims, No Drawings

PROCESS FOR PRODUCING AROMATIC HYDROCARBONS FROM CARBON MONOXIDE AND WATER

CROSS-REFERENCE TO RELATED APPLICATION

This application is a continuation-in-part application of U.S. Ser. No. 331,160, filed Dec. 16, 1981 now abandoned.

BACKGROUND OF THE INVENTION

1. Field of the Invention

The Kolbel-Engelhardt synthesis is a well-known process for producing liquid and gaseous hydrocarbons, including hydrocarbon fuels. (See *Brennstoff Chemie.*, Vol. 33 (1952) PA 13-21). In the process, mixtures of carbon monoxide and steam are usually contacted with an iron-based catalyst producing a broad range of linear and branched olefins and paraffins of $C_5$-$C_{20}$ carbon number. A particularly valuable portion of the produced hydrocarbons, produced under conditions of excess hydrogen, is the $C_6$-$C_{13}$ fraction, containing linear and branched paraffins, which is useful for internal combustion engines.

In this area, it is a general goal to improve the selectivity of the process in producing aromatic hydrocarbons for use in the chemical industry, and in particular, to improve the aromatic content of the $C_6$-$C_{13}$ hydrocarbon fraction, especially with respect to $C_6$-$C_9$ aromatic hydrocarbons in order to improve the octane number. It is known that use of $C_6$-$C_9$ aromatic hydrocarbons improves the octane number and is environmentally advantageous since it obviates the need for supplementary refining runs, as now practiced, to produce current nonleaded motor gasoline.

French Pat. No. 635,950 (1927) discloses a number of Fischer-Tropsch catalysts containing copper, silver, gold, zinc or Group VIII metals, or combinations thereof, for carrying out the conversion of mixtures of CO and $H_2$ to hydrocarbons. Also described is the use of cadmium or thallium, as equivalent promoters, in combination with the Group VIII metals, including cobalt and iron, for reducing soot formation. However, no specific mention is made of the use of thallium in particularly promoting the selectivity of an iron catalyst in the Kolbel-Engelhardt process toward the production of $C_6$-$C_{11}$ liquid aromatic hydrocarbons, substantially containing $C_6$-$C_9$ aromatics.

There is a continuing search for new and more efficient iron-based catalysts, which are inexpensive and convenient to prepare, for carrying out the Kolbel-Engelhardt process. Particularly, what is desired are iron-based catalysts which, under mild process conditions, exhibit greater selectivity to the formation of $C_6$-$C_{13}$ liquid hydrocarbons, and particularly, $C_6$-$C_{13}$ aromatic hydrocarbons containing a significant weight percentage of $C_6$-$C_9$ aromatic hydrocarbons.

SUMMARY OF THE INVENTION

We have unexpectedly found that a composition comprising a mixture of iron compounds and thallium compounds is an efficient catalyst for promoting the production of $C_6$-$C_{13}$ liquid aromatic hydrocarbons and particularly $C_6$-$C_9$ aromatic hydrocarbons in the Kolbel-Engelhardt process under mild conditions of temperature and pressure, and high carbon monoxide conversion efficiencies. Generally, the $C_6$-$C_{13}$ liquid hydrocarbons, produced by the above-described catalyst, comprise at least about 5 weight percent and greater of $C_6$-$C_{13}$ liquid aromatic hydrocarbons, and substantially comprising $C_6$-$C_9$ liquid aromatic hydrocarbons. The process can be conducted at relatively low temperatures, 230° to 350° C.; low pressure, from 1 to 10 atmospheres (0.1 to 1 MPa) and at carbon monoxide conversion efficiencies of about 30 to 80 percent to products.

The catalyst composition contains compounds of iron and thallium in an iron/thallium weight ratio of 100:1 to 1:100, respectively, taken as the free metals, and the composition can be supported or unsupported and contain catalyst promoter agents and additives as well. In a preferred embodiment, the iron value in the composition is substantially in the trivalent state wherein the thallium value is substantially deposited thereon.

In accordance with this invention, there is provided a process for producing liquid hydrocarbons, including those in the $C_6$-$C_{13}$ range, comprising contacting a mixture of carbon monoxide and water vapor, in a 5:1 to 1:5 volume ratio, respectively, with a supported or unsupported catalyst composition, which can be unpromoted or promoted with an agent other than copper or its compounds, comprising a mixture of iron compounds and thallium compounds, said iron value initially being substantially in the trivalent state prior to pretreatment, said thallium compounds being substantially impregnated on the surface of said catalyst composition which is pretreated at 270° C. or above, with a gaseous reducing atmosphere, wherein the weight ratio of iron/thallium, taken as the free metals, is from about 100:1 to 1:100, said process being conducted at a temperature of about 250° C. to 550° C. a pressure of about 0.1 to 7.5 MPa, and a space velocity of about 10 to 10,000 v/v/hr., thereby resulting in product liquid hydrocarbons in the $C_6$-$C_{13}$ range, comprising a substantial amount of $C_6$-$C_{13}$ aromatic hydrocarbons.

DESCRIPTION OF THE INVENTION AND PREFERRED EMBODIMENTS

The subject invention process is very useful in that it is capable of converting carbon monoxide and steam to $C_6$-$C_{13}$ liquid hydrocarbons, under mild conditions, unexpectedly containing a high percentage of $C_6$-$C_{13}$ aromatic hydrocarbons. Further, the composition of the obtained aromatic hydrocarbons is heavily skewed in the $C_6$-$C_9$ carbon range, which are extremely effective as chemical intermediates and as octane-increasing agents for motor gasoline. The reason why the combination of iron/thallium in the catalyst composition is unique in producing these results is not at all clear.

The catalyst composition is a subject of U.S. Pat. No. 4,436,834, and completely discloses the catalyst composition, properties thereof, methods of preparation, additives and promoter agents that can be utilized, and is hereby incorporated by reference for this purpose.

The catalyst composition comprises a mixture of iron compounds and thallium compounds, wherein the weight ratio of iron/thallium, taken as the free metals, is about 100:1 to 1:100. Also, the iron value is regarded as being initially substantially in the trivalent state. This is based on the fact that use of ferric compounds in the composition and use of an oxidizing atmosphere, e.g., air, in the drying step during preparation of the compounds lead to desired results. Other materials, known in the art as being promoters, activators, supports and catalytic-aiding materials may also be present, as long as the unique capability of the catalyst in producing $C_6$–$C_{13}$ aromatic hydrocarbons is not adversely affected. By the term "mixture of iron compounds and thallium compounds" is meant a physical admixture, solid solution, alloy, spinel, or new compound formed from the compounds, in which the compounds can be simply combined, precipitated individually and then combined, or formed by impregnating one solid compound with a solution of another, to produce the composition in which the thallium is substantially on the catalyst surface.

The weight ratio of iron/thallium, taken as the free metals, and referred to herein as Fe/Tl, being in parts by weight, in the composition is from 100:1 to 1:100, preferably from 100:5 to 65:35, and most preferred from about 100:5 to 80:20, respectively.

The catalyst composition preferably contains iron initially substantially in its trivalent state in order to convert CO and water vapor to $C_6$–$C_{13}$ aromatic hydrocarbons, and by the term "substantially" is meant at least about two-thirds of the iron present, such as in the case of $Fe_3O_4$. It is to be understood that an iron-based catalyst which is subjected to oxidizing conditions prior to CO hydrogenation with steam, such that a significant amount of ferric ion is formed on the catalyst surface, is also regarded as being an operable embodiment and included within the scope of the subject catalyst.

Iron compounds and thallium compounds operable in the composition are inorganic or organometallic and include their oxides, hydroxides, carbides, nitrates, carbonates, halides, sulfates and the like, and mixtures thereof. Representative examples include $Fe_2O_3$, $Fe_3O_4$, $Fe(OH)_3$, $Fe_3C$, $Fe(NO_3)_3$, $Fe_2(CO_3)_3$, $FeCl_3$, $Fe(NH_4)(SO_4)_2$, $Tl_2O$, $Tl(NO_3)_3$, $TlNO_3$, $Tl_2CO_3$, $Tl_2SO_4$, $TlCl_3$, $TlCl$, $TlF$ and the like. Preferred compounds are iron oxide, thallium oxide, thallium chloride, thallium fluoride, thallium nitrate, or mixtures thereof. Also preferred are where said iron compounds contain iron value substantially in the trivalent state. Also operable are organo-metallic compounds of iron/thallium which decompose to the respective oxides under the process conditions, e.g., thallium acetate and iron oxalate. Preferably, the thallium value is substantially impregnated on the surface of the catalyst composition.

Particularly preferred compounds are the oxides of the two metals, which can be formed, for example, by precipitating the metal values from aqueous solution of their soluble nitrates or sulfates by the addition of a base to form the respective hydrated oxides, which are dried and heated in the presence of air and converted to the metallic oxides. Thus, a preferred composition is a mixture of iron oxide and thallium oxide. If the drying step is conducted under vacuum or, in the absence of air with ferric ion being present, thallium nitrate is regarded as being the form of thallium initially in the catalyst. However, mixtures of thallium nitrate and thallium oxide are probably present and are regarded as such within the scope of this invention.

The catalyst composition can be supported or unsupported and is preferably supported. This preference is because the supported catalyst has in general, a longer catalyst lifetime and a lesser tendency to disintegrate during continued operation. Representative examples of supports include alumina, alkali-doped alumina, silica, titanium dioxide, magnesium oxide, magnesium carbonate, magnesium silicate, silicon carbide, zirconia, Kieselguhr, talc, clay and the like. By the term "alkali-doped alumina", as used herein, is meant a mixture of alumina and about 1 to 20 mole percent of an alkali metal salt, based on the moles of alumina, such as potassium carbonate, potassium silicate, cesium carbonate and the like. Mixtures of supports can also be utilized, including those above, for example, alumina and magnesium oxide. Preferred supports for the catalyst in the process for producing $C_6$–$C_{13}$ aromatic hydrocarbons, include cesium-doped alumina, or alumina, magnesium oxide, or mixtures thereof.

The amount of said support present can be from about 50 to 99 weight percent, based on the weight of said iron/thallium compounds, preferably 75 to 95 weight percent.

Various additives and promoter agents can also be utilized with the catalyst including cobalt, zinc, magnesium, nickel, chromium, manganese, zirconium, vanadium, tantalum, molybdenum, aluminum, titanium, alkali metals, alkaline earth metals, rare earth including actinides and lanthanides, and ammonium compounds, and compounds or salts thereof, and mixtures thereof such as cobalt oxide, zinc oxide, chromium oxide, and the like, which increase the activity and selectivity of the catalyst and thus reduce the required temperature in the process. Specifically excluded as promoter agents are copper and its compounds, salts, or the free metal. Also operable are alkali metal salts and alkaline earth metal salts, such as potassium salts, e.g., potassium carbonate, potassium oxide, potassium bicarbonate, potassium hydroxide, rubidium carbonate, barium carbonate, alkali metal borates and silicates; other metals such as zirconium, cerium, vanadium, rare earth elements, tantalum and molybdenum, and halide salts, e.g., fluoride, heated in the presence of air and converted to the metallic oxides. Thus, a preferred composition is a mixture of iron oxide and thallium oxide. Salts such as ammonium fluoride, potassium fluoride, and the like, also may be present for promoting the formation of aromatic hydrocarbons. In addition, other additives/promoters can be used including, but not limited to, alumina, manganese oxide, magnesium oxide, thorium oxide, calcium oxide, titanium dioxide, and the like, to help maintain the stability and integrity of the catalyst. Preferred promoters for the catalyst are cobalt, zinc, magnesium, as their salts of oxides, ammonium fluoride, potassium carbonate or mixtures thereof.

Amounts of promoters or additives that can be used in the compositions are from about 1 to 200 weight percent based on the weight of iron, taken as the free metals.

For example, cesium, as the carbonate salt, is used in about a 1 to 25 weight percent, cesium taken as the metal, to dope an alumina carrier. Ammonium fluoride is used in about a 0.1 to 10 weight percent, based on the weight of iron as the free metal, as a promoter, and potassium carbonate is used in about a 0.1 to 5 weight percent, based on the weight of iron, as the free metal, to promote the subject composition. Cobalt and zinc, as their salts or oxides, are used in a 1 to 20 weight percent, based on the weight of iron, as the free metal, to promote the catalyst.

Representative examples of catalyst compositions are (giving the composition and the weight ratio of the metals or elements in the free state) $Fe_2O_3/Tl_2O$ (10:1 Fe/Tl); $Fe_2O_3/Tl_2O/NH_4F$ (100:10:2 Fe/Tl/F); $Fe_2O_3/Tl_2O/K_2CO_3$ (100:10:1 Fe/Tl/K); $Fe_3O_4/Tl_2O$ (10:1 Fe/Tl); $Fe_2O_3/TlNO_3$ (10:1 Fe/Tl); $Fe_2O_3/CoO/TlNO_3$ (100:52.3:10 Fe/Co/Tl); and $Fe_2O_3/ZnO/TlNO_3$ (100:52.3:10 Fe/Zn/Tl).

A preferred catalyst composition useful in the process is an iron oxide/thallium oxide on cesium-doped alumina, wherein cesium is present, taken as the metal, in about 13 weight percent of the alumina present; iron, as the free metal, is present in about 10 weight percent of the combined weight of the cesium-doped alumina, and thallium is present, taken as the metal, in about 10 to 20 weight percent of the iron.

The catalyst composition can be made by a variety of techniques. The simplest method is to simply mix together an iron compound and a thallium compound, which are finely ground, in the proper weight ratio and utilizing the catalyst as is.

To insure a highly active catalyst, it is preferable to remove any excess alkali salts that might be initially present on the surface of iron hydroxide. Also, ion exchange agents, such as soluble ammonium compounds, can be used to wash the precipitated iron hydroxide. Alternatively, an ammonium salt such as ammonium bicarbonate can be used to precipitate the metal hydroxide from the solution.

A still further method of making the catalyst composition is to precipitate one metal value from an aqueous solution of its salts by the addition of base, or adjustment of the pH of the solution, and to isolate the metal oxide itself. The same procedure is then used for the other metal value and the two resulting metal oxides are mixed together to form the subject catalyst.

A particularly preferred method for making the iron-thallium catalyst is via the "incipient wetness" impregnation technique whereby a known amount of thallium salt, such as thallium nitrate, is dissolved in distilled water and added dropwise with thorough stirring to finely divided solid, water-insoluble iron compound to insure even dispersion on the solid surface of the thallium salt. Uniform distribution is insured by adding only just enough thallium solution to wet the entire surface of the iron solid to take advantage of surface spreading forces.

Also particularly preferred, is where the thallium compound is substantially impregnated on the surface of the catalyst composition. The resulting solid can be air-dried at room temperature, vacuum-dried at elevated temperature, or preferably heat-dried in air, and then ground into a fine particle size and used as is in the process.

The obtained catalyst composition generally has a surface area from about 5 to 300 m²/gm and preferably from about 10 to 250 m²/gm. After pretreatment in the process with a mixture of CO and $H_2$, the catalyst surface area reduces to about 5 to 50 m²/gm.

The invention process is conducted by contacting a mixture of carbon monoxide and water vapor with a supported or unsupported catalyst composition comprising a mixture of iron compounds and thallium compounds wherein the ratio of iron/thallium, taken as the free metals, is from about 100:1 to 1:100.

By the term "mixture of carbon monoxide and water vapor" is meant that other gases may also be present, for example, hydrogen, nitrogen, argon, carbon dioxide and the like. An inert gas, such as nitrogen or argon, can be used as a carrier gas for the feedstream.

The volume ratio of CO and water vapor in the process is about 5:1 to 1:5, preferably 2:1 to 1:2, and particularly preferred about 1:1. Water vapor is substantially steam under the process conditions.

The temperature of the process is conducted at about 230° to 550° C., preferably about 250° to 350° C., and particularly preferred about 275° to 350° C.

The pressure of the $CO/H_2O$ vapor feedstream in the process is about 0.1 MPa to about 7.5 MPa (1 to 75 atmospheres) and preferably about 0.5 to 1.5 MPa, and particularly preferred about 0.8 MPa.

The space velocity of the $CO/H_2O$ vapor feedstream is maintained at about 10 to 10,000 v/v/hr., preferably about 100 to 2500 v/v/hr., and particularly preferred at about 150 to 1500 v/v/hr.

A particularly preferred embodiment of the subject process comprises contacting a mixture of CO and water vapor in about a 2:1 to 1:2 volume ratio, respectively, with a supported catalyst composition comprising a mixture of iron oxide and thallium nitrate or oxide, the weight ratio of iron/thallium, taken as the free metals in the composition, being from about 100:5 to 65:35. The iron oxide of the catalyst composition preferably contains initially iron value substantially in the trivalent state, and thallium compound is preferably substantially impregnated on the surface of the catalyst composition, which is supported on aluminum oxide, magnesium oxide, or mixtures thereof. The process is conducted at a temperature of about 275° to 350° C., a pressure of about 0.5 to 1.5 MPa, and a space velocity of about 150 to 1500 v/v/hr., thereby resulting in product liquid hydrocarbons in the $C_6$–$C_{13}$ range comprising about 10 weight percent and higher of $C_6$–$C_{13}$ aromatic hydrocarbons. A particularly preferred embodiment is where the $C_6$–$C_{13}$ aromatic hydrocarbons comprise about 30 weight percent, and higher, $C_6$–$C_9$ aromatic hydrocarbons.

The apparatus which is used for the process can be any of the conventional types, wherein the catalyst is used in the form of a fixed bed, fluid bed, slurry and the like. Preferred is the catalyst in the form of a fixed or fluid bed.

The process is generally conducted by placing the catalyst composition into the reaction zone of the reactor and pretreating the catalyst prior to the run. The pretreatment step, as described hereinabove, can be conducted by passing a reducing gas such as $H_2$, CO, or $NH_3$ or mixtures thereof, either simultaneously or sequentially over the catalyst, at elevated temperature, for a certain period of time, which is dependent upon the amount of catalyst used, type of reactor and the like. During this pretreatment step, the catalyst is contacted with a reducing atmosphere, which is believed to convert some of the metal oxides to metal carbides, carbonitrides, and the like, or the reduced metal, as shown by X-ray analysis. The exact composition of the catalyst during the actual run is not known and actually may be continuously changing in nature during the run. It is, however, believed that iron is in the trivalent state substantially during the initial stages of the process.

After the pretreatment step, the temperature and pressure are adjusted to the desired ranges, and the feedstream comprised of carbon monoxide and water vapor is passed into the catalyst zone for reaction.

The hydrocarbons produced in the process comprise gaseous $C_1$–$C_4$ hydrocarbons and $C_5$–$C_{20}$ liquid hydrocarbons, including linear and branched paraffins and olefins. The liquid hydrocarbons produced usually comprise about 50 weight percent of the total hydrocarbons produced, generally about 25 weight percent and preferably 50 to 75 weight percent are comprised of $C_6$–$C_{13}$ hydrocarbons. The $C_6$–$C_{13}$ fraction generally contains at least about 5 weight percent, preferably 10 weight percent, or greater, of single ring aromatic $C_6$–$C_{13}$ hydrocarbons, and of this fraction, generally about 30 weight percent and preferably 50 to 80 weight percent, or greater, comprise $C_6$–$C_9$ aromatic hydrocarbons. By the term "substantial amount of $C_6$–$C_{13}$ aromatic hydrocarbons" is meant that at least about 5 weight percent of the $C_6$–$C_{13}$ hydrocarbons are $C_6$–$C_{13}$ aromatics.

By the term "substantial amount of $C_6$–$C_9$ aromatic hydrocarbons" is meant that the $C_6$–$C_9$ aromatic hydrocarbons produced comprise about 25 weight percent and higher, and preferably 50 to 90 weight percent of the $C_6$–$C_{13}$ aromatic hydrocarbons. However, depending upon the particular process conditions used, higher or lower amounts of the above-stated hydrocarbon products may be formed.

Methods of collecting and separating the obtained hydrocarbons are conventional and include atmospheric and reduced pressure distillation.

The "selectivity" in the process for producing aromatic hydrocarbons is expressed as a weight percentage of a particular total carbon fraction that comprises aromatic hydrocarbons. For example, the selectivity of the process to $C_6$–$C_{13}$ aromatic hydrocarbons is the weight percent of the entire $C_6$–$C_{13}$ liquid hydrocarbon fraction obtained that are $C_6$–$C_{13}$ single ring aromatics.

The following comparative example and examples illustrate the subject matter which we regard as our invention and the example is illustrative of the best mode of carrying out the invention, as contemplated by us, and should not be construed as being limitations on the scope and spirit of the instant invention.

EXAMPLE 1

Preparation of the Catalyst 10:1 Fe/Tl (Catalyst Two)

To a boiling solution of 404 g. ferric nitrate nonahydrate in 1.5 liters of distilled water was added, with stirring, a solution of 237 g. ammonium bicarbonate dissolved in 1.5 liters water resulting in the precipitation of iron oxide. The resulting solution was kept boiling until all $CO_2$ evolution had ceased. The precipitate was filtered, washed with distilled water until the wash water was neutral. The washed solid was dried in a vacuum at 100° C. for 12 hours. The resulting solid was impregnated by the technique of incipient wetness by the dropwise addition to the solid of a solution of 7.3 g. thallium nitrate in 70 ml. of water. The ferric oxide adsorbed practically all of the solution. The impregnated solid was dried in a vacuum oven at 110° C. for 12 hours. The resulting impregnated solid weighed 86 g. and analyzed for 10 parts by weight iron, per 1 part thallium, taken as the free metals.

EXAMPLE 2

The 10:1 Fe/Tl catalyst, prepared by the incipient wetness technique, as described above in Example 1, was tested by the following procedure for hydrocarbon synthesis.

The catalyst was tested in a fixed bed, tubular reactor fitted with a highly conductive brass sleeve. Catalyst pretreatment consisted of flowing a mixture of $H_2/CO/N_2$ (49:50:1, by volume, approx.) over the catalyst at 270° C., 1 atm. pressure, and a space velocity of about 480 v/v/hr. for about 18 hours. At the end of this pretreatment, the temperature was reset to about 250° C. and the pressure raised to 8.2 atmospheres. The space velocity of the feedstream was adjusted to 400 v/v/hr., which consisted of a feed of about 3:1 $CO/H_2O$ obtained by passing a CO feedstream through a steam vessel at 25 cc/min. and heated at 121° C. wherein the vapor pressure of water was about 2.0 atm. (equilibrium steam vapor pressure). However, it is felt that equilibrium conditions were not obtained and that the feedstream was about 4 to 5:1 $CO/H_2O$.

Liquid samples were collected at 4° C. and gas analyses were performed by in-line gas chromatography. A highly conductive brass sleeve was placed in the ¾-inch space between the surrounding furnace and the ½-inch O.D. stainless steel, 5-inch long reactor tube. This presumably has two favorable effects: (1) it tends to reduce axial temperature gradients; and (2) it normalizes and dissipates temperature gradients created by heats of reaction. A traveling, 1/16-inch thermocouple positioned in a ⅛-inch O.D. stainless steel tube at the reactor center, indicated that the axial temperature gradients in the reactor were reduced to 1° C./cm up to 300° C. and to about 2.5° C./cm up to 350° C.

The run, at 250° C., was continued for 24 hours and the analytical results are listed below in Table I.

In a second run, the catalyst was tested at 300° C., all other conditions being substantially identical to the 250° C. run, and during which the pressure, at the same settings for CO/steam feed, rose from 8.2 to 9.9 atm. The products were collected over a 24-hour period. The results of this run are also listed in Table I below.

TABLE I

|  | 250° C. | 300° C. |
| --- | --- | --- |
| CO Conversion | 33% | 78% |
| Selectivity to $CO_2$ | 75% | 52% |
| Hydrocarbon Selectivity | 25% | 48% |
| Methane (As % of TOT HC) | 2.1% | 1.2% |
| $C_1$–$C_5$ (As % of TOT HC) | 23.5% | 19.8% |
| $C_1$–$C_{13}$ (As % of TOT HC) | 51.8% | 66.1% |
| $C_{13}+$ (As % of TOT HC) | 24.7% | 14.1% |
| Single Ring Aromatics (As % of TOT HC) | 5.9% | 13.4% |
| Single Ring Aromatics in $C_6$–$C_{13}$ | 11.4% | 20.3% |
| % Aromatics in: |  |  |
| $C_6$ Fraction | 3.7% | 16.9% |
| $C_7$ Fraction | 13.9% | 30.0% |
| $C_8$ Fraction | 20.7% | 29.1% |
| $C_9$ Fraction | 16.4% | 28.0% |
| $C_{10}$ Fraction | 6.7% | 12.2% |
| $C_{11}$ Fraction | 7.8% | 8.8% |
| $C_{12}$ Fraction | 7.8% | 10.9% |
| $C_{13}$ Fraction | 6.1% | 4.8% |

What is claimed is:

1. A process for producing liquid hydrocarbons, including those in the $C_6$–$C_{13}$ range, comprising contacting a mixture of carbon monoxide and water vapor, in a 5:1 to 1:5 volume ratio, respectively, with a catalyst composition, which can be unpromoted or promoted with an agent other than copper or its compounds, wherein said catalyst consists essentially of a mixture of iron compounds and thallium compounds being supported or unsupported, said compound of iron and thallium being selected from the group consisting of an oxide, hydroxide, carbonate, sulfate, carbide, halide, nitrate, or mixtures thereof, wherein said iron compound contains iron value initially being substantially in the trivalent state prior to pretreatment, said thallium compounds being substantially impregnated on the surface of said iron compound, which is pretreated at 270° C. or above, with a gaseous reducing atmosphere, wherein the weight ratio of iron/thallium, taken as the free metals, is from about 100:1 to 1:100, said process being conducted at a temperature of about 250° C. to 550° C. a pressure of about 0.1 to 7.5 MPa, and a space velocity of about 10 to 10,000 v/v/hr., thereby resulting in product liquid hydrocarbons in the $C_6$–$C_{13}$ range, comprising a substantial amount of $C_6$–$C_{13}$ aromatic hydrocarbons.

2. The process of claim 1 wherein said product $C_6$–$C_{13}$ hydrocarbons comprise at least about 5 weight percent of $C_6$–$C_{13}$ aromatic hydrocarbons.

3. The process of claim 2 wherein said product $C_6$–$C_{13}$ hydrocarbons comprise about 10 weight percent and higher $C_6$–$C_{13}$ aromatic hydrocarbons.

4. The process of claim 1 wherein said $C_6$–$C_{13}$ aromatic hydrocarbons comprise about 30 weight percent and higher $C_6$–$C_9$ aromatic hydrocarbons.

5. The process of claim 1 wherein the weight ratio of iron/thallium, taken as the free metals, is from about 100:5 to about 65:35.

6. The process of claim 1 wherein said catalyst is supported on $Al_2O_3$, alkali-doped $Al_2O_3$, $SiO_2$, $TiO_2$, MgO, $MgCO_3$, silicon carbide, zirconia, or mixtures thereof.

7. The process of claim 1 wherein said iron compound is iron oxide.

8. The process of claim 1 wherein said thallium compound is thallium oxide, thallium chloride, thallium fluoride, thallium nitrate, or mixtures thereof.

9. The process of claim 1 wherein said catalyst composition further contains a promoter agent.

10. The process of claim 9 wherein said promoter agent is selected from compounds or free metals of cobalt, zinc, mangesium, nickel, chromium, manganese, alkali metals, alkaline earth metals, zirconium, vanadium, tantalum, molybdenum, aluminum, titanium, rare earth metals including actinides and lanthanides, ammonium compounds, or mixtures thereof.

11. The process of claim 10, wherein said promoter agent is selected from cobalt, zinc, chromium, manganese, barium, as their salts or oxides, ammonium fluoride, potassium carbonate, or mixtures thereof.

12. The process of claim 1 wherein the mixture of CO and water vapor in a volume ratio of about 2:1 to 1:2, respectively.

13. The process of claim 1 wherein said temperature is about 250° to 350° C.

14. The process of claim 1 wherein said pressure is about 0.5 to 1.5 MPa.

15. The process of claim 1 wherein said catalyst is in the form of a fixed bed.

16. The process of claim 1 wherein said catalyst is in the form of a fluid bed.

17. The process of claim 1 wherein said catalyst is in the form of a slurry.

18. A process for producing liquid hydrocarbons, including those in the $C_6$–$C_{13}$ hydrocarbon range, comprising contacting a mixture of CO and water vapor in about 2:1 to 1:2 volume ratio, respectively, with a catalyst composition initially comprising a mixutre of ferric oxide and thallium nitrate or oxide, and promoted with a promoter agent other than copper, said promoter being selected from the group consisting of cobalt, zinc, chromium, manganese, barium, as their salts or oxides, ammonium fluoride, potassium carbonate, or mixtures thereof, prior to pretreatment, at 270° C. or above, with a reducing gaseous mixture containing carbon monoxide and hydrogen, the weight ratio of iron/thallium, taken as the free metals, in the composition, being from about 100:5 to 65:35, said thallium compound being substantially impregnated on the surface of said iron compound, said process being conducted at a temperature of about 250° to 350° C., a pressure of about 0.5 to 1.5 MPa, and a space velocity of about 150 to 1500 v/v/hr, thereby resulting in product $C_6$–$C_{13}$ hydrocarbons comprising about 10 weight percent of $C_6$–$C_{13}$ aromatic hydrocarbons, which are comprised of at least about 10 weight percent and higher $C_6$–$C_9$ aromatic hydrocarbons.

* * * * *